United States Patent
Rivas

(10) Patent No.: US 10,828,341 B2
(45) Date of Patent: Nov. 10, 2020

(54) METHOD FOR PREPARATION OF PHARMACOLOGICALLY-RELEVANT COMPOUNDS FROM BOTANICAL SOURCES

(71) Applicant: Jose Rivas, San Francisco, CA (US)

(72) Inventor: Jose Rivas, San Francisco, CA (US)

( * ) Notice: Subject to any disclaimer, the term of this patent is extended or adjusted under 35 U.S.C. 154(b) by 599 days.

(21) Appl. No.: 15/490,806

(22) Filed: Apr. 18, 2017

(65) Prior Publication Data

US 2018/0296616 A1   Oct. 18, 2018

(51) Int. Cl.
*A61K 36/185* (2006.01)

(52) U.S. Cl.
CPC ........ *A61K 36/185* (2013.01); *A61K 2236/13* (2013.01); *A61K 2236/15* (2013.01); *A61K 2236/31* (2013.01); *A61K 2236/37* (2013.01); *A61K 2236/39* (2013.01)

(58) Field of Classification Search
None
See application file for complete search history.

(56) References Cited

U.S. PATENT DOCUMENTS

| | | | |
|---|---|---|---|
| 7,001,629 B1 | 2/2006 | Mengal et al. | |
| 16,550,150 * | 8/2019 | Rivas .................. | A61K 36/185 424/725 |
| 2004/0033280 A1* | 2/2004 | Whittle ................ | A61K 31/352 424/774 |
| 2004/0147767 A1 | 7/2004 | Whittle et al. | |
| 2010/0062121 A1 | 3/2010 | Farid et al. | |
| 2015/0119592 A1 | 4/2015 | Hamler et al. | |
| 2015/0126754 A1* | 5/2015 | Fernandez Cid .... | A61K 31/352 549/391 |
| 2018/0214790 A1 | 8/2018 | Tucker | |

OTHER PUBLICATIONS

Fazlali, et al., American Journal of Essential Oils and Natural Products, 3:46. (Year: 2015).*
International Search Report received in International Application No. PCT/US18/37950 dated Sep. 18, 2018, 3 pages.
Frequently Asked Questions, Dec. 15, 2016, located at: https://www.popecannabisdistillation.com/faq/.
EOV2000 the Unique Receiver, Jan. 1, 2017, located at: https://www.heartmagic.com/NewReceiver.html.
Does anyone have any suggestions for the removal of chlorophyll and waxes from a hexane leaf extract? May 5, 2014, located at: https://www.researchgate.net/post/Does_anyone_have_any_suggestions_for_the_removal_of_chlorophyll_and_waxes_from_a_hexane_leaf_extract.
Medical Benefits of Terpenes, Apr. 4, 2017, located at: https://prohbtd.com/watch/learn/episodes/what-are-terpenes/.

* cited by examiner

*Primary Examiner* — Michael Barker
(74) *Attorney, Agent, or Firm* — Law Office of Christopher Peil

(57) ABSTRACT

In a multi-step process for selectively purifying various pharmacologically-relevant components of a source plant such as *cannabis*, an initial step of the process provides a low-temperature, robust essential oil/terpene capture that also dehydrates and decarboxylates the starting product—fresh raw *cannabis*—by means of a vacuum-assisted microwave distillation process. By doing the terpene capture under vacuum distillation temperature may be kept low. The low distillation temperature maximizes yields of thermally-sensitive components such as terpenes and cannabinoids. The process includes additional steps of: extract cannabinoids from the dehydrated *cannabis* to produce a crude extract via a supercritical CO2 extraction process; purify crude extract of fats, lipids, plant material; and distill relevant cannabinoids from the purified crude extract via a wiped-film process. Selected terpenes and cannabinoids are then recombined in predetermined proportions to achieve extracts of unusual purity and having targeted therapeutic profiles.

20 Claims, 7 Drawing Sheets

METHOD FOR PREPARATION OF PHARMACOLOGICALLY-RELEVANT COMPOUNDS FROM BOTANICAL SOURCES

BACKGROUND

Technical Field

The present disclosure relates to methods for preparing extracts of botanical products. More particularly the present disclosure relates to methods for preparing a purified extract from fresh *cannabis*.

Background Information

A plant medicine's therapeutic activity is attributed to the active constituents it contains. Although there are examples that show the activity of C. *Sativa* has been linked to specific chemical species, it is also true that the plant's medicinal affect is due to one or more combinations of constituents acting in concert.

*Cannabis* contains approximately 500 natural compounds. The two classes of compounds of greatest medicinal value are terpenes and cannabinoids. While *cannabis* may contain literally hundreds of terpenes, only a few have caught the interest of researchers and practitioners, among them: myrcene, linalool, limonene, humulene, pinene and caryophyllene. Until recently, it was thought that terpenes functioned mostly to give *cannabis* strains their characteristic flavors and aromas. Because of this, it was thought that, in preparing extracts, it wasn't necessary to be concerned about terpene content in a final product because the terpenes didn't appear to be important to the medicinal effect of the product.

Recent research has revealed that terpenes play a much greater role in the effect of a particular *cannabis* strain than originally thought. It has been found, for example, that in many situations, the interaction between a terpene molecule and a cannabinoid molecule is determinative of the final effect of the relevant strain, with the terpene, in effect, regulating the medicinal action of the cannabinoid. Thus, a new appreciation is developing for terpenes' contribution to the medicinal effect produced by a particular *cannabis* strain.

Over 100 cannabinoids have been identified in *cannabis*, some of which are psychoactive. Of the cannabinoids, the molecules most studied may be tetrahydrocannabinol (THC) and cannabidiol (CBD), the two cannabinoids accounting for the largest portion of the plant's extract. While THC may account for more than 20% of extract volume in a high-THC strain, CBD levels of over 4% are considered to be high. Recent research has shown CBD to have analgesic, anti-inflammatory, and anti-anxiety properties without the psychoactive effects associated with THC.

Current methods of preparing abstracts fail to appreciate the importance of terpenes to the quality and efficacy of the final product. Further, the cannabinoid yield from conventional methods tends to be sub-optimal. Additionally, the time required for conventional methods places a limit on the amount of extract that can be produced in an economic manner.

SUMMARY

In a multi-step process for selectively purifying various pharmacologically-relevant components of a source plant such as *cannabis*, an initial step of the process provides a low-temperature, robust essential oil/terpene capture that also dehydrates and decarboxylates the starting product—fresh raw *cannabis*—by means of a vacuum-assisted microwave distillation process. By doing the terpene capture under vacuum distillation temperature may be kept low. The low distillation temperature maximizes yields of thermally-sensitive components such as terpenes and cannabinoids.

The process includes additional steps of:
  extract cannabinoids from the dehydrated *cannabis* to produce a crude extract via a solvent extraction process;
  purify crude extract of fats, lipids, plant material via a winterization process;
  distill relevant cannabinoids from the purified crude extract via a wiped-film process.

Selected terpenes and cannabinoids are then recombined in predetermined proportions to achieve extracts of unusual purity and having targeted therapeutic profiles.

DETAILED DESCRIPTION

Figure 1:
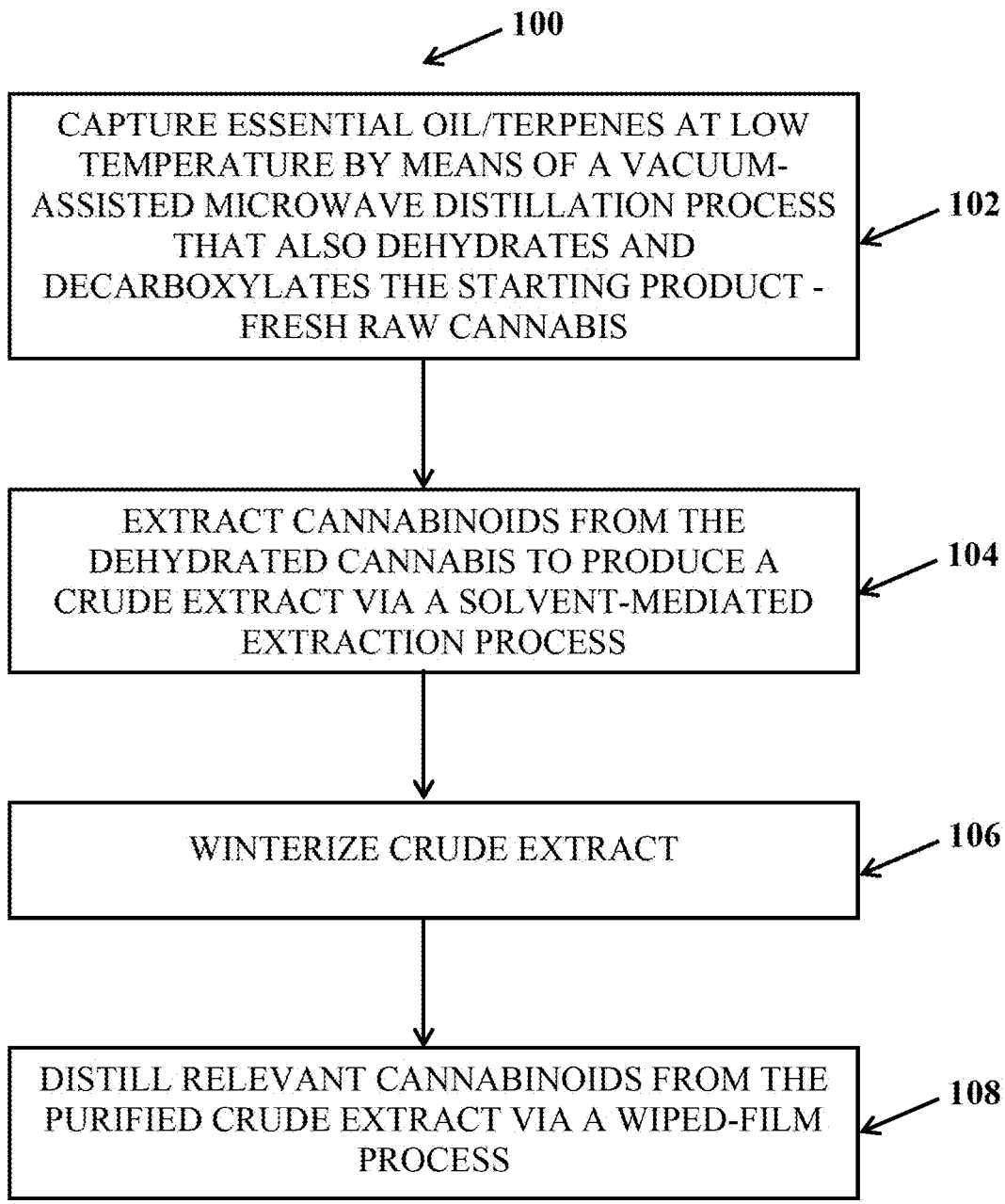
FIG. 1 provides a block a diagram of a process for preparing a purified extract from raw, fresh *cannabis*.

In a multi-step process 100 for selectively purifying various pharmacologically-relevant components of a source plant such as *cannabis*, an initial step 102 of the process provides a low-temperature, robust essential oil/terpene capture that also dehydrates and decarboxylates the starting product—fresh raw *cannabis*—by means of a vacuum-assisted, gravity-assisted microwave distillation process. By doing the terpene capture under vacuum, distillation temperature may be kept low. The low distillation temperature maximizes yields of thermally-sensitive components such as terpenes and cannabinoids.

The process includes additional steps of:
  extract cannabinoids from the dehydrated *cannabis* to produce a crude extract via a solvent-mediated extraction process 104;
  purify crude extract of fats, lipids, plant material 106; and
  distill relevant cannabinoids from the purified crude extract via a wiped-film process 108.

Selected terpenes and cannabinoids are then recombined in predetermined proportions to achieve extracts of unusual purity and having targeted therapeutic profiles.

Terpene Distillation: Rapid Material Dehydration and Cannabinoid Decarboxylation in a Single Process For the initial distillation, a vacuum assisted microwave hydro-distillation (VAMHD) process is employed to rapidly dehydrate fresh plant material at significantly lower temperatures than normally possible with conventional processes, distilling the terpenes and decarboxylating the cannabinoids contained in the plant material.

Conventionally, great emphasis is placed on drying *cannabis* slowly and gradually to preserve the terpene and cannabinoid content. Cut stems of *cannabis* are typically hung or the buds are trimmed and laid out on drying racks in climate-controlled environments. This drying/curing process can take up to four weeks. As part of an industrial-scale process, the time and space requirements for such gradual drying and curing add significantly to the manufacturing cost of the final product.

There exist high-speed methods of drying. Oven drying and convection drying have been used to shorten the time required to dry *cannabis*. Significant economies of time have been achieved with such speed-drying methods. But the high temperatures required adversely affect the terpene and cannabinoid content, resulting in an inferior quality final product.

Microwave drying has also been used. But it is thought that microwave drying seriously compromises the concentration of psychoactive components in the *cannabis*, resulting in an inferior-quality final product.

After *cannabis* has been dried, it must be decarboxylated to activate the psychoactive components. The main *cannabis*-derived cannabinoids come from related cannabinoid acids, which are 2-carboxylic acids, composed of a carboxyl group linked at the alpha carbon of the main cannabinoid group. While cannabinoid acids do have some therapeutic uses, in order to produce the psychoactive effect for which *cannabis* is so highly valued, the raw cannabinoid acids must be decarboxylated, usually through heating, to remove the carboxyl (—COOH) functional group at the alpha carbon to form cannabinols or cannabidiols. Conventionally, *cannabis* is decarboxylated by heating the raw *cannabis* to approximately 200° F. (~93° C.) for approximately one hour. While the prolonged exposure to high temperature converts the cannabinoids to a biologically-active form, it also has the unfortunate effect of significantly decreasing cannabinoid concentration because of the vulnerability of the cannabinoid molecule to thermal degradation. Furthermore, this step allows the achievement of greater purity in each of the downstream processes described herein below.

Lower temperatures may be used for decarboxylation, but the process proceeds much more slowly. In fact, *cannabis* can be decarboxylated merely by allowing it to cure at room temperature for an extended period of time—several weeks, for example. Thus, an industrial-scale producer is faced with choosing between a time-intensive process and one that adversely affects the quality of the end product.

The process herein described utilizes vacuum-assisted microwave hydro distillation (VAMHD) to dry and decarboxylate the fresh plant material, which allows the it to be rapidly dehydrated and decarboxylated at significantly lower temperatures of approximately 10-50° C., thus preserving the terpene and cannabinoid profile of the original material, while saving approximately 10 days over the industry drying standard.

Figure 2:
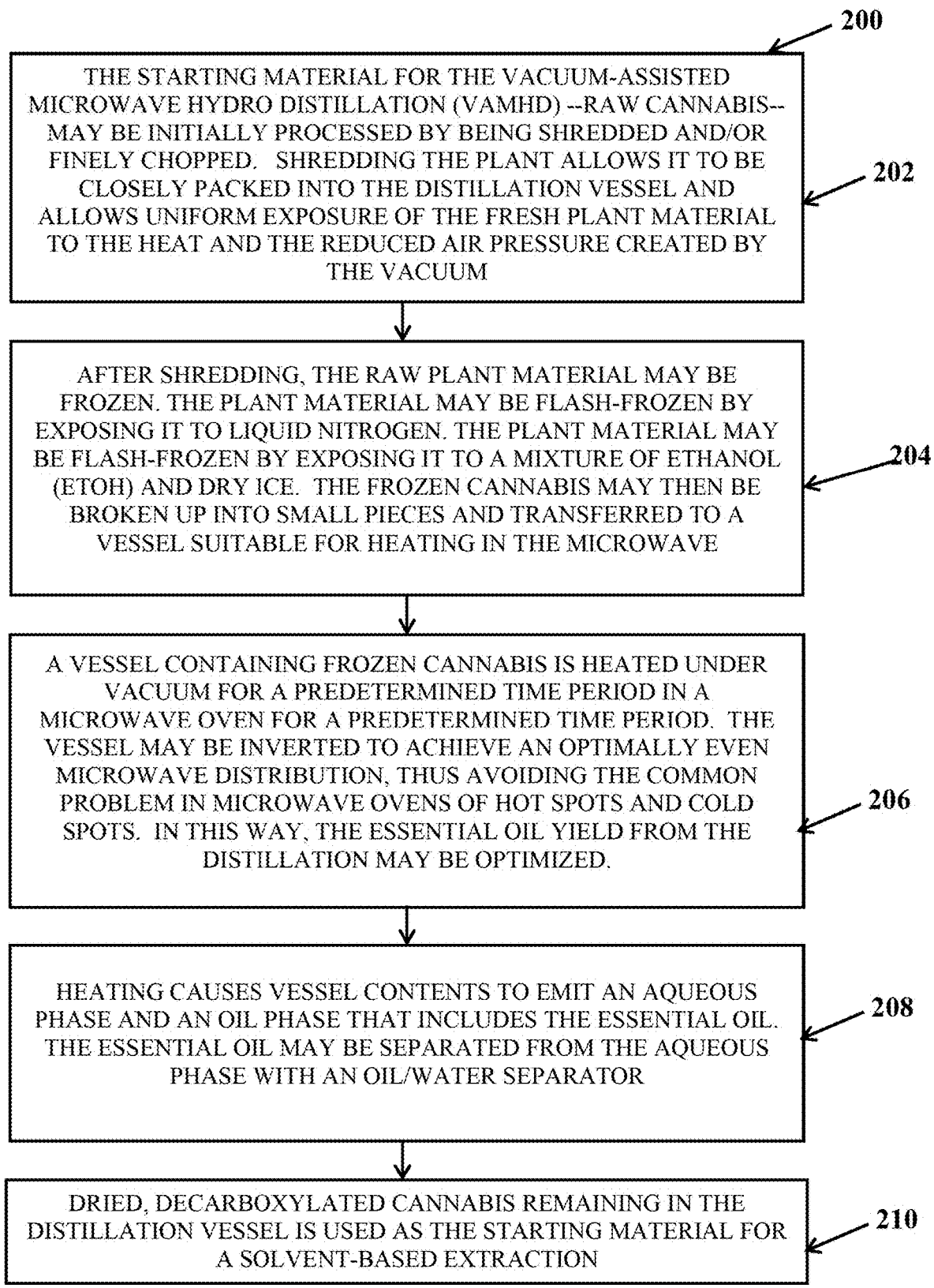
FIG. 2 provides a block diagram of a sub-process for extracting natural essential oils from raw fresh *cannabis*.

FIG. 2 shows a sub-process of terpenes/essential oil capture 200. As shown in FIG. 2, the starting material for the vacuum-assisted microwave hydro-distillation (VAMHD) is raw *cannabis*—that is, freshly-harvested plant material that has not had an opportunity to dry.

Hydro distillation is an alternative method of extracting essential oils to steam distillation. In hydro distillation, rather than having steam pass through the plant material from which the essential oil is to be extracted, the plant material is soaked in water for a period of time, after which the mixture of water and plant material is heated. The volatile essential oil is carried away in the steam, condensed and separated.

The fresh plants may be initially processed by being shredded and/or finely chopped 202. Shredding the plant allows it to be closely packed into the distillation vessel 304 and allows uniform exposure of the fresh plant material to the heat and the reduced air pressure created by the vacuum 312.

After shredding, the raw plant material may be frozen 204. In embodiments, the plant material may be flash-frozen by exposing it to liquid nitrogen. In embodiments, the plant material may be flash-frozen by exposing it to dry ice. The frozen *cannabis* may then be broken up into small pieces and transferred to a vessel suitable for heating in the microwave. In embodiments, a round-bottom flask, such as a 3-liter round-bottom flask, may be used.

Additionally, the fresh plant material may be placed in the distillation vessel 304 without being previously frozen.

If dried plant material is being used, an amount of water may then be added to the distillation vessel 304 containing the raw plant material to prepare the mixture.

One of ordinary skill will appreciate that the process is readily scaled and that the choice of vessel is a function of the process scale.

The vessel containing *cannabis*/water mixture may then be placed into a microwave oven under vacuum 312. In embodiments, the vessel containing the frozen *cannabis* is then heated for a predetermined time period. The length of the time period is a function of the wattage of the microwave oven, the size of the vessel and the quantity of *cannabis* in the vessel. In embodiments, a 3-liter vessel packed with frozen *cannabis* may be heated on 'high' in a 1000 watt microwave oven for 60 minutes 206. In embodiments, the vessel may be inverted to achieve an optimally even microwave distribution, thus avoiding the common problem in microwave ovens of hot spots and cold spots. In this way, the essential oil yield from the distillation may be optimized.

Throughout the heating period, the vessel contents emit a vapor that includes an aqueous phase and an oil phase, containing the essential oil from the *cannabis*, containing a high concentration of terpenes 208.

As indicated above, the end products of the distillation sub-process are *cannabis* essential oil and dried, decarboxylated *cannabis*. The dried, decarboxylated *cannabis* may then undergo a secondary solvent extraction to recover the biologically active cannabinoids 210.

Figure 3:
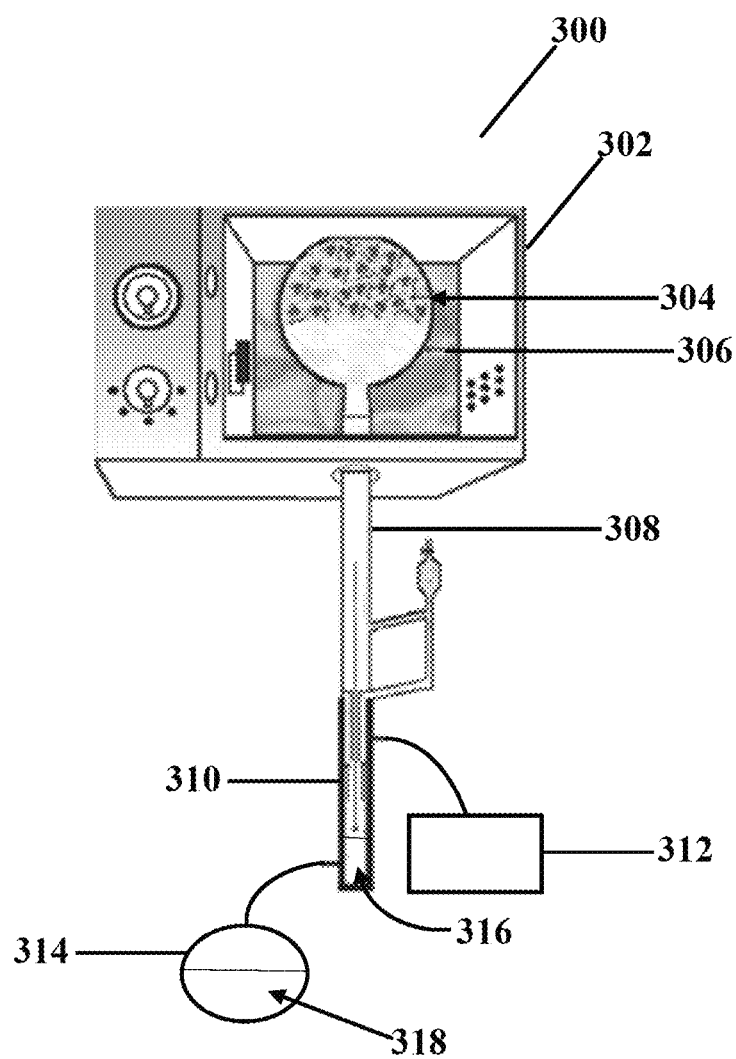
FIG. 3 provides a diagram of a system for extracting natural essential oils from raw fresh *cannabis*.

FIG. 3 provides a diagram of a vacuum-assisted microwave dehydration system 300 with which the sub-process of FIG. 2 may be carried out. As shown, the system 300 includes a microwave heating unit 302. The exemplary embodiment of FIG. 3 shows a conventional microwave oven 302 as would be found in many households and laboratory settings. Depending on the process scale, the microwave oven 302 could be a larger, higher-power, industrial-scale unit.

A distillation vessel 306 is packed with *cannabis* 304 prepared as described herein above and placed in the microwave oven 302. A water-chilled condenser 308 is coupled with the neck of the distillation vessel 306. It should be noted that the distillation vessel 307 and the condenser 308 are shown in an inverted position. In embodiments, the sub-process 200 is gravity-assisted. As the *cannabis* 304 heats, the essential oil and the water form a mixed vapor. It will be appreciated that performing the process 200 under vacuum conditions considerably reduces the temperature at which the essential oil and water within the distillation vessel are converted to their vapor phases. The mixed vapor, due to the vacuum conditions, is promptly evacuated from the vessel 306, being drawn from the vessel 306 into the condenser 308. By exploiting the effect of gravity, evaporated water and essential oil are separated from *cannabis* 304 in the vessel 306 much more rapidly than would be possible without the gravity assist. Furthermore, the gravity greatly assists drying of the *cannabis* to prepare for the following sub-process. The vacuum conditions, supplemented by the gravity assist, also allow recovery of a greater quantity of essential oil, having a richer concentration of terpenes.

By using a gravity assist to continuously evacuate essential oil/water from the distillation vessel, it is possible to dry and carboxylate the *cannabis*. In fact, at the end of the distillation, the *cannabis* 306 remaining in the vessel 306 is nearly completely dried, needing only a short exposure to the air at room temperature to finish drying. Laboratory testing of the extract reveals that the cannabinoid fraction of the extract is 97% decarboxylated cannabinoids.

Vacuum conditions are maintained within the system 300 by means of a vacuum generator 312.

An oil/water separator 310 facilitates separation of the essential oil 316 and the aqueous component 318 into separate phases. The essential oil then accumulates in the separator 310, while the aqueous component 318 is drained into a separate vessel 314.

Secondary Solvent Extraction

Figure 4:
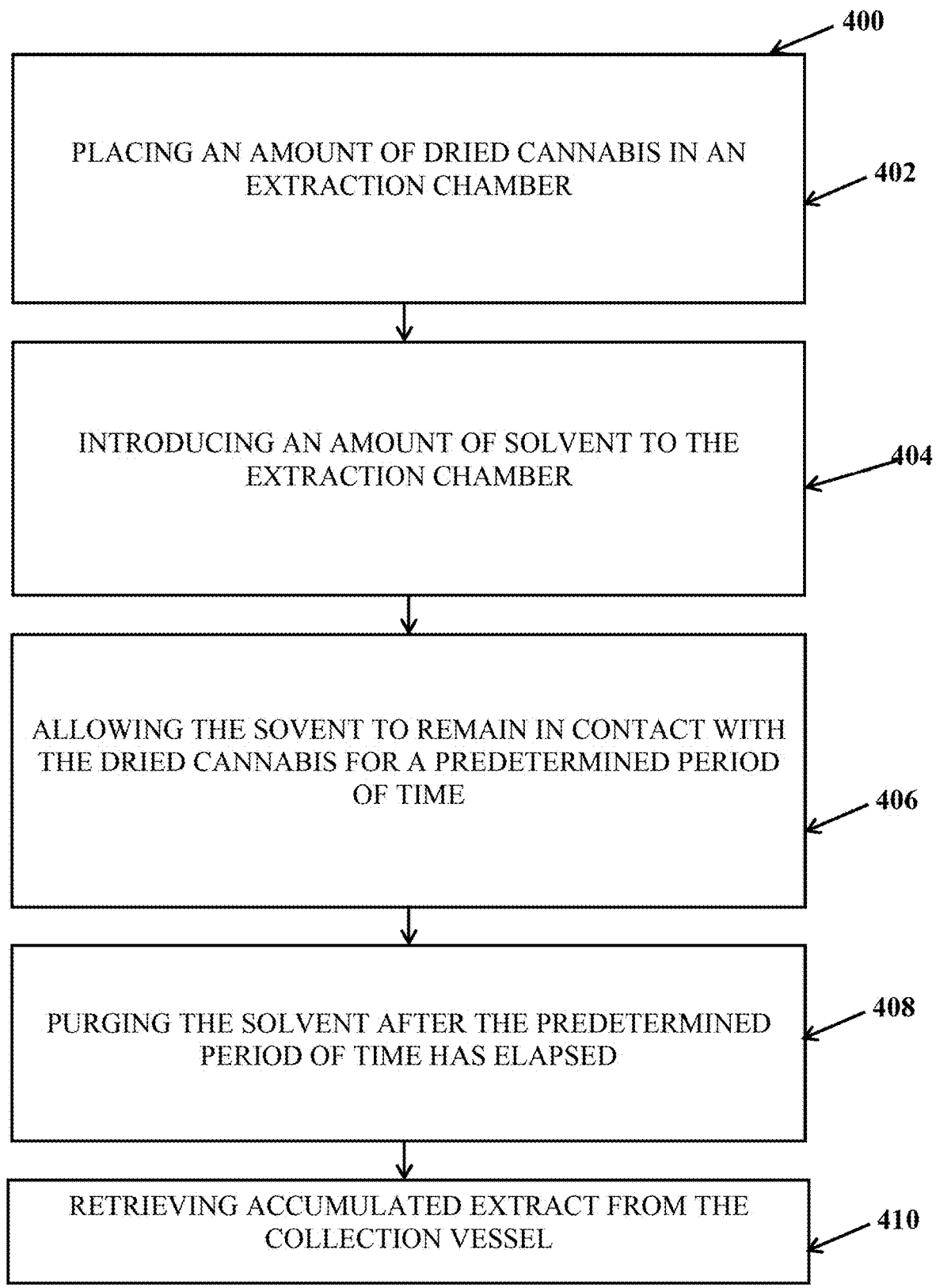
FIG. 4 provides a block diagram of a sub-process for extracting relevant cannabinoids from dehydrated *cannabis*.

As in FIG. 4, a further step in the process involves a secondary solvent extraction 400 for relevant cannabinoids. This process may utilize any number of hydrocarbon solvents having a polarity sufficient for cannabinoid extraction including, but not limited to, methanol, ethanol, isopropanol, hexane, pentane, butane, propane, naphtha, chloroform. Supercritical CO2 may also be used for the solvent extraction.

While naphtha or petroleum ether extract may well be the most effective solvents for most cannabinoids, concerns about toxic solvent residues in products have caused practitioners to look for additional solutions. In embodiments, supercritical CO2 extraction is used to produce a crude extract containing the relevant cannabinoids from the dried, decarboxylated *cannabis* because it is an efficient, non-toxic and non-flammable process.

Extraction relies on the phenomenon of diffusion, in which the solvent diffuses into the solid plant matter and the target material diffuses from the plant matter into the solvent. Diffusion may occur at different rates with different solvents. For example, extraction with hydrocarbon solvents may require a period of hours.

Diffusion may occur faster when using supercritical fluids than with hydrocarbon solvents, allowing extraction to proceed more rapidly, taking an hour or less, depending on the type of product, the quantity and the equipment. While supercritical CO2 extraction provides certain advantages, it is also a much more costly process.

Thus, a sub-process for extracting cannabinoids from dried *cannabis* 400 may include steps of:
  placing an amount of dried *cannabis* in an extraction chamber 402;
  introducing an amount of solvent to the extraction chamber 404;
  allowing the solvent to remain in contact with the dried *cannabis* for a predetermined period of time 406;
  purging the solvent from the extraction chamber after the predetermined period of time has elapsed 408; and
  retrieving accumulated extract from the collection vessel 410.

Supercritical CO2 Extraction

A supercritical fluid can diffuse through a solid as a gas does, and can also dissolve materials as a liquid does. In addition, close to the critical point, small changes in pressure and/or temperature lead to relatively large changes in density of the supercritical fluid, allowing many properties of a supercritical fluid to be adjusted or "tuned" to fit the application. For these reasons, supercritical fluids, such as supercritical CO2, can substitute for hydrocarbon solvents in many industrial and laboratory processes, such as cannabinoid extraction.

Figure 5:
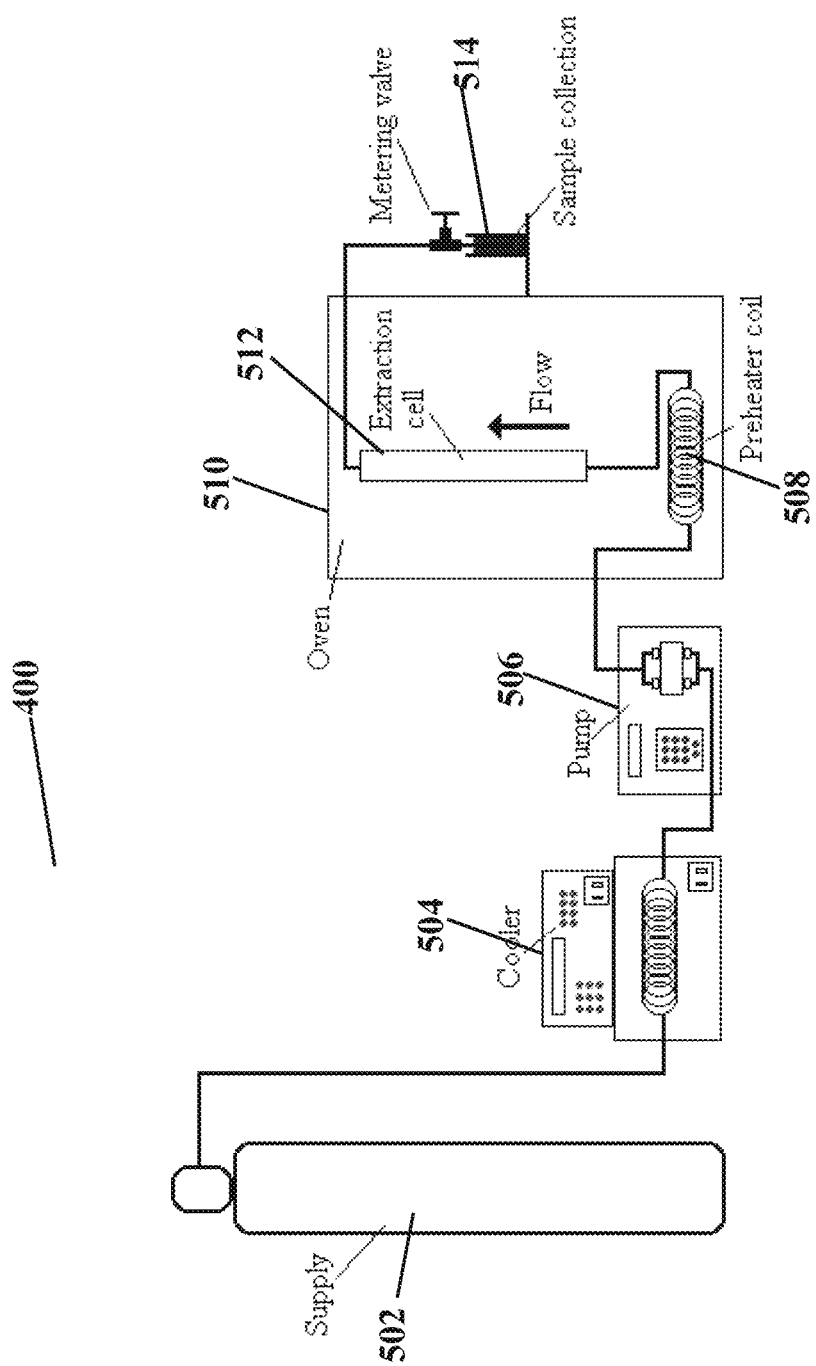
FIG. 5 provides a diagram of a system for extracting relevant cannabinoids from dehydrated *cannabis*.
Figure 6:
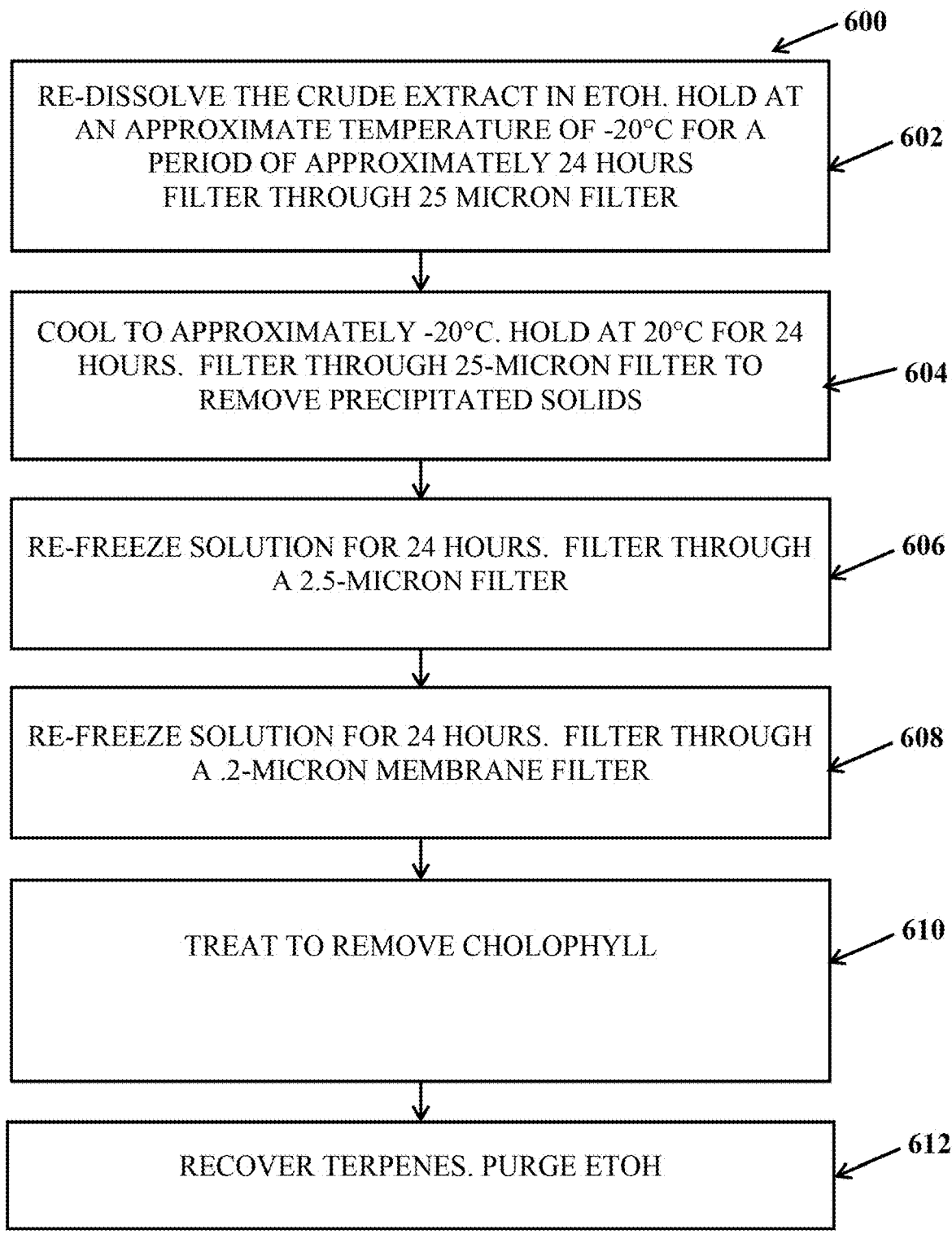
FIG. 6 provides a block diagram of a sub-process for refining a *cannabis* extract.

Referring now to FIG. 5, shown is an exemplary system 500 for solvent extraction. The system 500 may include a solvent supply 502, typically in the form of a supply tank containing solvent or compressed CO2. A line may conduct the solvent from the supply 502 to a reservoir 504. The solvent then proceeds to a pump 506 which pumps the solvent to a heating zone 510, where it is heated to the lowest temperature conducive to dissolution of the cannabinoids in the solvent. Using the lowest effective temperature lessens the possibility of diminished yield due to thermal damage to the cannabinoids.

After passing through a heater coil 508, the heated solvent passes into an extraction vessel 512. In the extraction vessel 512, the solvent diffuses through the plant matter of the *cannabis* and dissolves the target material to be extracted— in this case, the cannabinoids. The dissolved cannabinoids and lipids are cleared from the extraction vessel 512 into a collection vessel 514 by means of a metering valve.

The product resulting from the solvent extraction is a crude *cannabis* extract containing a high concentration of cannabinoids, with some side products, such as lipids and pigments from the *cannabis*.

Subsequent refinement steps may be a function of the extraction method utilized. Supercritical CO2 extractions may be followed by a winterizing step, described in detail, herein below, which leverages ethanol (ETOH) to separate pure cannabinoids and terpenes from other byproducts isolated during extraction. This process serves to pull out undesired material in advance of downstream processing.

A hydrocarbon solvent-based extraction, due to the polarity of the solvent, does not incorporate the plant waxes and fats found in a CO2 extract. Thus, an activated carbon filtration process may be used to remove undesirable compounds like chlorophyll and other pigments.

Winterization

As above, the product of the secondary extraction is a crude extract having a high concentration of cannabinoids. In addition to the cannabinoids, the extract may also contain residual terpenes that were not extracted during the initial process. The crude extract may also contain a number of undesirable components such as lipids, waxes, pigments, or other such plant material. An additional refinement process serves to greatly reduce the level of these undesirable components and prepare the crude extract for downstream processing.

Many of the impurities remaining in the extract may be longer-chain hydrocarbons having a relatively high melting point. Thus, a refining procedure to remove the long-chain impurities involves dissolving the crude extract in ethanol (ETOH), freezing the ETOH solution and filtering it to remove the precipitated long-chain impurities. Additionally, treating the crude extract with ETOH, freezing and filtering have the added benefit of removing more of the residual terpenes and further concentrating the cannabinoid fraction.

The initial step in the winterization process 600 involves re-dissolving the crude extract in ETOH 602. In embodiments, the ETOH may be at room temperature. In embodiments, to facilitate dissolving the crude oil in the ETOH, the ETOH may be heated to a temperature slightly above room temperature (RT), for example 30° C. While a lower temperature helps to ensure a higher cannabinoid concentration in the final product, in certain applications, it may be desirable to heat the ETOH considerably above RT, for example, as high as 45° C.

In embodiments, the crude oil and the ETOH may be combined in a predetermined ratio, for example 10 ml of ETOH for each gram of extract. Choice of the ration of oil to ETOH is driven by a number of factors, such as lipid and cannabinoid concentration of the starting material.

After the ETOH and the crude oil are combined, the mixture may be stirred, either manually, using a laboratory implement such as a spatula, or by using an automated stirring device, such as a magnetic stirrer. After the crude oil is fully dissolved in the ETOH, the solution is held at an approximate temperature of −20° C. for a period of approximately 24 hours 602. The solution is then passed through a filter having a 25-micron pore size to remove precipitated solids.

The solution may again be chilled to −20° C., and held for 24 hours 604. It will be appreciated that freezing the solution for an extended period results in a liquid layer—the extract/ethanol solution and a layer of precipitated solids. Found within the precipitated solids are the plant matter and solidified lipid impurities that are to be eliminated from the solution. Following the 24-hour freeze, the solution is passed through a 25-micron filter.

The solution may again be refrozen to −20° C. and held for 24 hours 606, after which it may be passed through a 2.5 micron filter.

The solution may again be refrozen to −20° C. and held for 24 hours 608, after which it may be passed through a 0.2 micron membrane filter.

It will be appreciated that the duration of the freezing periods may be reduced by subjecting the solution to lower temperatures. For example, if the solution is frozen using, for example, dry ice, the freezing time may be reduced. The freezing point of the solvent and/or the solute, would, of course, impose a lower limit on the freezing temperature.

Even after being thoroughly treated in this manner, there may remain enough chlorophyll in the solution to give it a green hue. In embodiments, the solution may, for example, be treated by exposing to sunlight or UV radiation, washing with an appropriate solvent or by an activated carbon filtration. Removing the chlorophyll, however, may adversely affect cannabinoid concentration in the final product 608.

The waxes removed from the oil as a result of winterization may be discarded, however they may also be recovered and diverted into other processes/products, skin care additives or personal lubricants, for example.

Terpenes removed as a result of winterization may be recovered and recombined with the terpenes produced as a result of the primary extraction for use in other products, or for recombining with the cannabinoids at predetermined levels to produce an extract having a targeted therapeutic profile 610.

After the waxes, pigments and plant material are removed during the winterization process, the ETOH may be purged from the solution 610, leaving a winterized extract. In embodiments, using a vacuum and a vacuum oven, the boiling point of the ETOH can be reduced to well below room temperature. In embodiments, the ETOH may be purged using a rotary evaporator.

Wiped-Film Distillation

The final stage of the disclosed method utilizes a wiped-film distillation technique to purify the winterized material into a distillate containing highly concentrated cannabinoids in ratios similar to those found in the original plant material. Purity is typically greater than 98% total cannabinoids and may be as high as 99.8% pure cannabinoids.

The winterized extract typically has a thick, syrupy consistency. Additionally, because of the high cannabinoid content, the extract is very heat-sensitive. Thus, it is desirable, at all stages of processing to minimize exposure of the extract to higher temperature. A conventional still-pot distillation provides a number of disadvantages for a heat-sensitive product such as the presently-described extract. Chief among these is the long residence time necessitated by the conventional pot distillation. As we have indicated, the extended thermal exposure in a batch process system degrades the quality of the extract. In particular, exposure of the cannabinoids in the extract to the extended heat in a conventional pot distillation system causes a significant drop in the cannabinoid concentration of the final product.

Another disadvantage of a conventional pot distillation system is that a large volume of product is lost due to the extract fouling the equipment as a result of its sticky, viscous consistency. As a matter of fact, the *cannabis* extract can foul the equipment so badly that it has to be discarded frequently.

Another disadvantage of a conventional pot distillation approach is the very slow rate of processing. The speed with which a quantity of extract can be distilled using a wiped-film approach produces a distinct business advantage for commercial producers.

Finally, as indicated above, the wiped-film approach allows the production of an extract of exceptional purity and potency.

In embodiments, this final distillation may utilize a wiped-film evaporator and vacuum distillation. In embodiments, this final distillation may utilize a short-path wiped-film evaporator having a condenser that is located inside the evaporator body.

A wiped film evaporator can provide the short residence time needed and an open, low pressure drop configuration, allowing continuous, reliable processing of heat sensitive, viscous, or fouling materials such as *cannabis* extract, without product degradation.

In a wiped-film evaporator (WFE), the product is fed into the top of a cylinder and evenly dispersed by a distributor. Heat is applied to the exterior surface of the cylinder, for example by a heated jacket. As the liquid film runs down the inside surface of the cylinder, a rotating wiper system spreads, agitates and moves the product down and off of the heated cylinder wall in a matter of seconds. Heat transfer under vacuum conditions causes the product to evaporate at a greatly reduced temperature. Evaporated product is allowed to pass through a liquid-vapor separator, while droplets of unevaporated product are thrown back to the heated surface. The vapor condenses on a condenser enclosed within the cylinder and exits the WFE through a distillate outlet.

In embodiments, condensation may take place in a condenser located outside of the evaporator.

The wiped-film distillation may be carried out using any of a number of commercially-available wiped-film, short-path stills. For example, in an embodiment, the wiped-film distillation may be carried out using a still such as the Pope Wiped-Film Molecular Still, manufactured by POPE SCIENTFIC, Inc., Saukville, Wis.

In embodiments, the wiped-film distillation may be carried out using a still such as a Thin-Film, Short-Path Evaporator manufactured by LCI, Inc. Charlotte, N.C.

In embodiments, the wiped-film distillation may be carried using a still such as a Short-Path Distillation Plant manufactured by ROOT SCIENCES, Inc., Seattle, Wash.

Any of the foregoing systems are vacuum distillation systems that embody the use of a wiped-film (aka "thin-film") evaporator having an incorporated condenser, which greatly reduces the amount of time the product is exposed to heat to no more than a few seconds. The provision of a short path between the evaporator and the condenser allows the pressure within the system to be kept at a level that approximates the vapor pressure of the cannabinoid fraction, allowing the cannabinoid fraction to evaporate rapidly with minimal application of heat, thereby preserving the cannabinoids.

While several commercially available systems have been described herein above, one of ordinary skill will readily realize that a system for wiped-film distillation system embodying the same operative principles as the named systems may be obtained from other sources or it may be constructed from readily available components, either of which embodiments are entirely consistent with the scope of the present disclosure and the attached claims.

Figure 7:
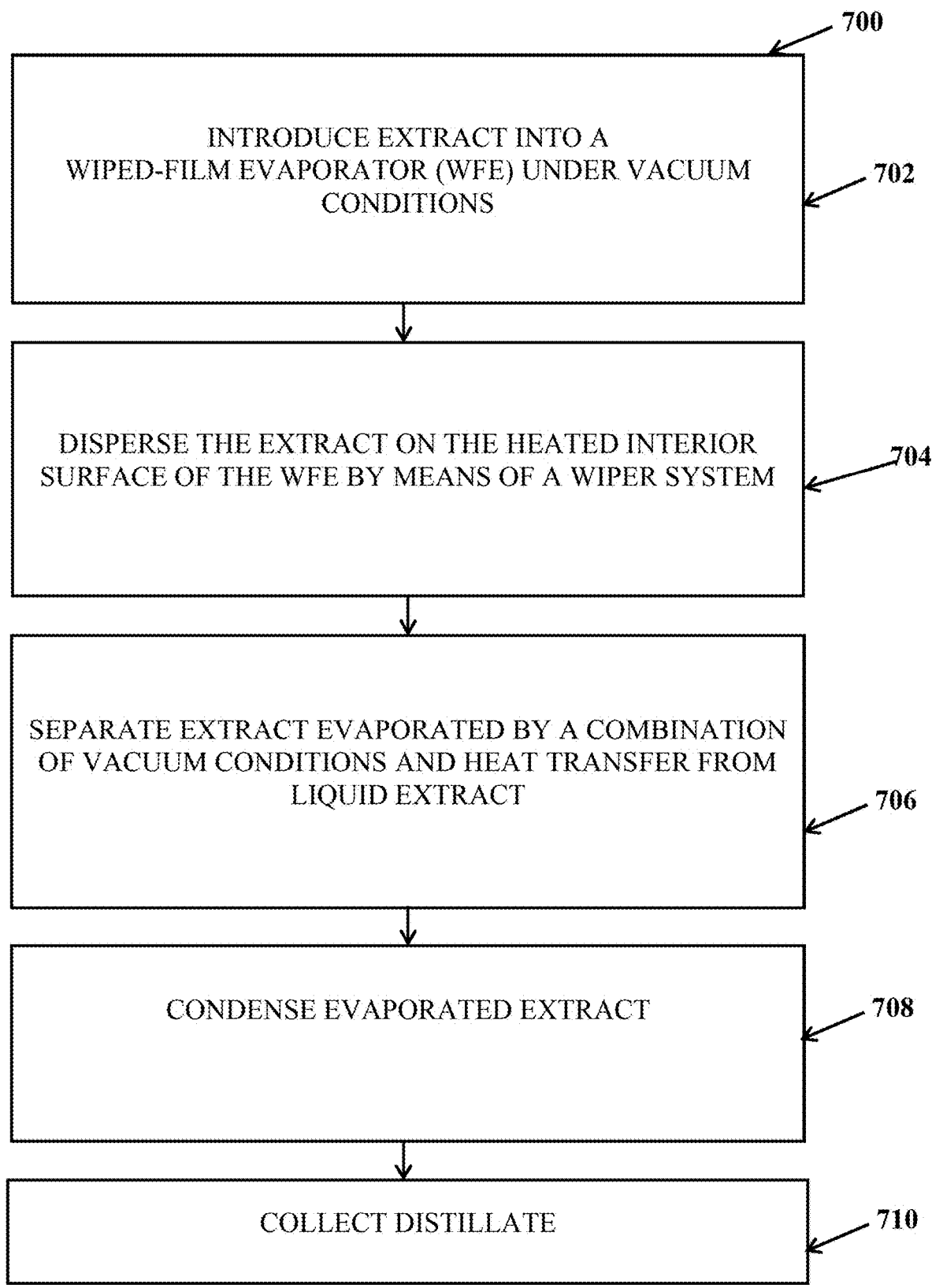
FIG. 7 provides a block diagram of a sub-process for preparing a distillate from refined *cannabis* extract.

FIG. 7 provides a block diagram of a sub-process for distilling a *cannabis* extract. As described herein above, the sub-process 700 may include at least the steps of:
  introducing liquid extract into a wiped-film evaporator (WFE) under vacuum conditions 702;
  dispersing the liquid extract on the heated interior surface of the WFE by means of a wiper system 704;
  separating extract evaporated by a combination of vacuum conditions and heat transfer from liquid extract 706;
  condensing evaporated extract 708; and
  collecting distillate 710.

The methods for preparing concentrated extracts of *cannabis* may be deployed at any scale. Small producers may utilize them to produce milliliter amounts of product. Furthermore, the process may be scaled and used by commercial producers to produce bulk quantities.

It will be appreciated that many products may result from the methods and approaches herein described. One product is a highly-purified, terpene-rich *cannabis* essential oil. A second product is a *cannabis* extract having a cannabinoid concentration that may exceed 99%. Many additional products may result from recombining the essential oil and cannabinoids in various proportions to produce extracts having a variety of medicinal effects. Furthermore, as a result of the ability to fine-tune the extraction sub-process by varying temperature and pressure, the extraction procedure may be modified to favor one cannabinoid fraction over another. Thus, the relative concentration of different cannabinoid fractions can be varied in the final extract.

Additionally, the by-products of the winterization process may themselves be diverted into other products, for example personal lubricants and skin-care products.

Moreover, the hydrosol resulting from the initial distillation may itself serve as the basis for additional products.

While the above methods have been described in connection with production of *cannabis* extract, the same methods may be deployed to isolate and purify components of all sorts of culinary, aromatic and medicinal herbs such as lavender, sage and rosemary.

While the foregoing written description enables one of ordinary skill to use the methods herein described, those of ordinary skill will understand and appreciate the existence of variations, combinations, and equivalents of the specific embodiments, methods, and examples herein. The specification should therefore not be limited by the above described embodiments, method, and examples, but by all embodiments and methods within the scope and spirit of the attached claims.

The invention claimed is:

1. A method for preparing purified extracts from raw *cannabis* comprising:
  A. distilling a terpene-rich essential oil from a water/raw *cannabis* mixture prepared by heating the raw *cannabis*/water mixture under gravity-assisted, continuing vacuum conditions in a microwave oven at a predetermined power level for a predetermined period of time;
  B. followed by preparing a cannabinoid-rich crude extract from dried, decarboxylated *cannabis* remaining after distillation by exposing the dried, decarboxylated *cannabis* to a solvent and allowing a resulting extract to accumulate in a collection vessel as the solvent is purged;
  C. followed by refining the crude extract to remove impurities; and
  D. followed by preparing a purified extract from the refined extract by distilling the refined extract in a wiped-film evaporator under vacuum conditions.

2. The method of claim 1, wherein raw *cannabis* comprises fresh plant material that has not had an opportunity to dry.

3. The method of claim 1, wherein A further comprises at least one of:
  shredding and/or chopping the raw *cannabis*;
  soaking the raw *cannabis* in water;
  freezing the raw *cannabis*;
  packing the raw *cannabis* into a distillation vessel.

4. The method of claim 1, wherein A further comprises:
  heating a distillation vessel containing raw *cannabis* in a microwave oven under vacuum conditions;
  inverting the distillation vessel as the *cannabis* is being heated;
  heating the *cannabis* in the microwave oven for a period of 60 minutes;
  heating the *cannabis* in a 1000-watt microwave oven at a 'high' power setting.

5. The method of claim 1, wherein A further comprises:
  condensing vapor produced by heating the *cannabis* into a mixture of terpene-rich *cannabis* essential oil and water
  separating the terpene-rich essential oil from the heated raw *cannabis*/water mixture;
  wherein heating in the microwave dries and decarboxylates the *cannabis*.

6. The method of claim 1, wherein the solvent comprises one of:
  methanol;
  ethanol;
  isopropanol;
  hexane;
  pentane;
  butane;
  propane;
  naphtha; and
  chloroform.

7. The method of claim 6, wherein C further comprises:
filtering the crude extract through activated carbon to remove undesirable components.

8. The method of claim 1, wherein the solvent comprises at least one of:
super-critical CO2.

9. The method of claim 1, wherein B further comprises:
placing an amount of dried *cannabis* in an extraction chamber;
introducing an amount of solvent to the extraction chamber;
allowing the solvent to remain in contact with the dried *cannabis* for a predetermined period of time;
allowing the solvent to evaporate after the predetermined period of time has elapsed; and
retrieving accumulated extract from the collection vessel.

10. The method of claim 9, wherein the predetermined period of time is approximately one hour.

11. The method of claim 8, wherein B further comprises:
varying temperature and/or pressure of the solvent to target an identified cannabinoid fraction for extraction.

12. The method of claim 1, wherein C further comprises:
preparing a refined extract from the crude extract by dissolving the crude extract in a solvent and iteratively:
chilling a resulting solution to a temperature of approximately −20° C. for a period of at least 24 hours; and
filtering out solid elements formed in the chilled solution.

13. The method of claim 1, wherein C further comprises:
dissolving the crude extract in ethanol;
alternately chilling the extract/ethanol solution to an approximate temperature of −20° C. for a period of approximately 24 hours and filtering the extract to remove precipitated solids;
wherein each said filtering is through a filter having a smaller pore size than a preceding filter.

14. The method of claim 13, wherein the frozen solids comprise undesirable compounds including lipids, waxes, pigments, and plant matter.

15. The method of claim 13, wherein C further comprises:
purging ethanol from the extract/ethanol solution.

16. The method of claim 13, wherein C further comprises:
treating the chilled, filtered extract/ethanol solution to remove pigments.

17. The method of claim 16, wherein treating the chilled, filtered extract/ethanol solution to remove pigments comprises one of:
filtering through activated charcoal; and
treating with UV light and/or sunlight.

18. The method of claim 1, wherein D further comprises:
introducing the refined extract into a wiped-film evaporator (WFE) under vacuum conditions;
dispersing the refined extract on the heated interior surface of the WFE by means of a wiper system;
separating the refined extract evaporated by a combination of vacuum conditions and heat transfer from liquid extract;
condensing evaporated extract; and
collecting condensed distillate.

19. The method of claim 18, wherein condensing is performed by one of:
an enclosed condenser; and
a condenser located outside of the WFE.

20. The method of claim 1, further comprising:
recombining the terpene-rich essential oil and the purified extract in predetermined portions to create products having targeted medicinal effects.

* * * * *